United States Patent [19]

Dye et al.

[11] 4,107,180

[45] Aug. 15, 1978

[54] SALTS OF ALKALI METAL ANIONS AND PROCESS OF PREPARING SAME

[75] Inventors: James L. Dye, East Lansing; Joseph M. Ceraso, Lansing, both of Mich.; Frederick J. Tehan, Utica, N.Y.; Mei Tak Lok, Urbana, Ill.

[73] Assignee: The United States of America as represented by the United States Department of Energy, Washington, D.C.

[21] Appl. No.: 528,381

[22] Filed: Nov. 29, 1974

[51] Int. Cl.$^2$ ............................ C07F 1/04; C07F 1/06
[52] U.S. Cl. .................................................. 260/338
[58] Field of Search ........................................ 260/338

[56] References Cited

PUBLICATIONS

Dye et al, J. Am. Chem. Soc., vol. 96, pp. 608–609 (1974).

Primary Examiner—Norma S. Milestone
Attorney, Agent, or Firm—Dean E. Carlson; Frank H. Jackson; James W. Weinberger

[57] ABSTRACT

Compounds of alkali metal anion salts of alkali metal cations in bicyclic polyoxadiamines are disclosed. The salts are prepared by contacting an excess of alkali metal with an alkali metal dissolving solution consisting of a bicyclic polyoxadiamine in a suitable solvent, and recovered by precipitation. The salts have a gold-color crystalline appearance and are stable in a vacuum at −10° C. and below.

9 Claims, No Drawings

SALTS OF ALKALI METAL ANIONS AND PROCESS OF PREPARING SAME

CONTRACTUAL ORIGIN OF THE INVENTION

The invention described herein was made in the course of, or under, a contract with the UNITED STATES ATOMIC ENERGY COMMISSION.

BACKGROUND OF THE INVENTION

This invention relates to compounds which are alkali metal anion salts of metal cations in bicyclic polyoxadiamines and to a method for their preparation.

The use of reducing agents is important in both organic and inorganic synthesis. Since most generally available reducing agents have but a single electron available, a free radical may form during synthesis which may lead to the formation of undesirable intermediate compounds in reactions requiring two electrons for completion. Solutions of salts of alkali anions can eliminate some of these problems, since the anions are two-electron reducing agents. The driving force for the reaction $M^- \rightleftarrows m^+ + 2e^-$ is very large and the stability of an intermediate state M is expected to be low. Therefore reactions which require two electrons for completion will be easier to carry out than with, for example, metal-ammonia solutions, which appear to go via one-electron steps with intermediate radical formation. The potential number of two electron reactions in both organic and inorganic synthesis is large and may include aromatic reductions, metal alkyl formation and reductions of transition metal complexes to low-valence states.

SUMMARY OF THE INVENTION

This invention relates to compounds of an alkali metal anion salt of an alkali metal cation in a bicyclic polyoxadiamine compound of the formula:

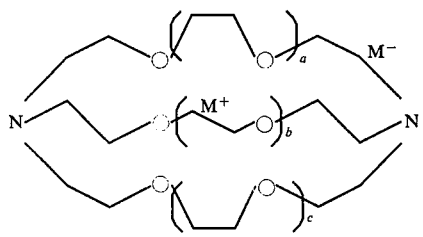

where M is an alkali metal, $M^+$ is a cation of an alkali metal, $M^-$ is an anion of an alkali metal and where $a$, $b$ and $c$ are integers from 0 to 2, which compound will react chemically as a two-electron reducing agent.

This invention also relates to a method for preparing the alkali metal anion salts of an alkali metal cation in a bicyclic polyoxadiamine compound, wherein a bicyclic polyoxadiamine compound having the formula:

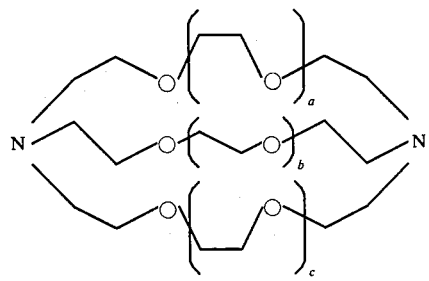

where $a$, $b$ and $c$ are integers from 0 to 2, is dissolved in a suitable solvent to form a metal dissolving solution, which is then cooled to below 10° C., and contacted with an excess of alkali metal which dissolves in the metal dissolving solution to form the anion salt, the solution is then warmed to 0° to 10° C., separated from the alkali metal and the alkali metal anion salt of the alkali metal cation in the bicyclic polyoxadiamine compound recovered.

It is therefore one object of this invention to provide a compound of an alkali metal anion.

It is a further object of this invention to provide a compound which is an alkali metal anion salt of an alkali metal cation in a bicyclic polyoxadiamine compound.

It is a further object of this invention to provide a compound which can react chemically as a two-electron reducing agent.

It is still another object of this invention to provide a method for preparing a compound of an alkali metal anion.

It is yet another object of this invention to provide a method for preparing a compound that is an alkali metal anion salt of an alkali metal cation in a bicyclic polyoxadiamine compound.

Finally, it is the object of this invention to provide a method for preparing a compound which can react chemically as a two-electron reducing agent.

BRIEF DESCRIPTION OF THE PREFERRED EMBODIMENT

These and other objects of the invention may be met by dissolving a bicyclic polyoxadiamine compound having the formula:

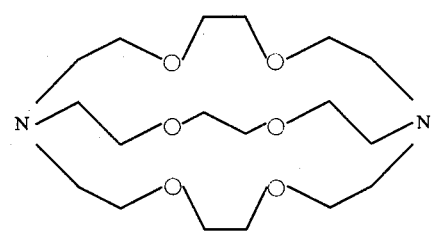

in a suitable solvent, said solvent being a nonreactive, donor solvent having a dielectric constant from 8 to 20, to form a metal dissolving solution containing about 0.2 M bicyclic compound, cooling the dissolving solution to from 10° to −60° C., contacting the cooled metal dissolving solution with an excess of alkali metal selected from the group consisting of sodium, potassium, rubidium, cesium and sodium and potassium until the solution is saturated with alkali metal, whereby the anion salt of an alkali metal is formed, warming the solution to 0° to 10° C., separating the metal dissolving solution from the alkali metal and recovering the alkali metal anion salt of the alkali metal cation in the bicyclic polyoxadiamine compound.

The bicyclic polyoxadiamine compounds as described and used herein have generally the formula:

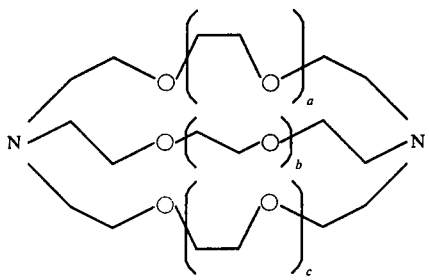

where $a$, $b$ and $c$ are integers from 0 to 2. Where all of the bicyclic compounds are useful for the alkali metal salts and method of preparing the same, the specific compound used for the reduction of this invention to practice was the bicyclic compound where $a$, $b$ and $c$ are 1. This compound has the empirical formula of $C_{18}H_{36}O_6N_2$ and the complete name of 4,7,13,16,21,24-hexaoxa-1,10-diazabicyclic (8,8,8) hexacosane and will be referred to hereinafter as (2,2,2-crypt). These bicyclic polyoxadiamine compounds act as complexing agents which tie up or "encrypt" the alkali metal cation within the compound. These compounds and their preparation are discussed in detail in *Tetrahedron Letters* 2885; 2889 (1969), B. Dietrich, J. M. Lehn and J. P. Sauvage.

A suitable solvent is a nonreactive, donor solvent having a dielectric constant of from 8 to 20 such as ethers, amines, including aliphatic amines, and polyethers. Specific examples of such suitable solvents are methylamine, ethylamine, ethylenediamine, tetrahydrofuran, 1,2-propane diamine and 1,3-propane diamine.

The metal dissolving solution may contain from 0.05 to about 0.2 M bicyclic polyoxadiamine while from about 0.1 to 0.2 M are preferred for best results.

The alkali metals from which anion salts may be prepared include sodium, potassium, rubidium and cesium. More than one alkali metal may be dissolved in the dissolving solution at one time such as, for example, a sodium-potassium alloy. In this example, a sodium anion salt of a potassium cation would be formed because of a greater affinity of the bicyclic compound for potassium. The amount of alkali metal which will dissolve in the metal dissolving solution is self-limiting and will depend upon the concentration of bicyclic polyoxadiamine compound, since only that amount will dissolve that can be tied up by the bicyclic compound. It is important that an excess of alkali metal be available and that the metal dissolving solution remain in contact for a sufficient time that the dissolving solution is saturated with alkali metal, in order that the anion salt is formed. Multiple contacts where the anion salt produced is recovered between contacts of alkali metal and dissolving solution may also be used to ensure the best yield of anion salt.

Contact temperature must be below about 10° C. to avoid decomposition of the anion salt as it is formed and temperatures as low as about −78° C. or dry ice temperatures were found satisfactory.

Once the metal dissolving solution is saturated with alkali metal, the solution is warmed to from about 0° to about 10° C. to ensure that all of the anion salt which has been formed is dissolved after which the dissolving solution is separated from contact with the alkali metal. After separation is complete, the anion salts may then be recovered from the solution.

Recovery of the anion salts from the metal dissolving solution may be accomplished by several methods, some dependent upon the alkali metal anion salt involved. For example, the sodium anion salt may be recovered by cooling the solution to at least −15° C. to precipitate the salt from the solution. Sodium anion salts may also be recovered by precipitation with another solvent such as diethyl ether or normal hexane or by evaporation of the dissolving metal solution solvent by low-temperature distillation. The rubidium salt has only to be recovered by solvent evaporation.

Once the anion salts have been separated from the dissolving solution, they may be washed, if necessary, to purify them of any adhering dissolving solution with diethyl ether or normal hexane. Once recovered, the salts may be stored indefinitely under a vacuum at −10° C.

The following examples are given as illustrative of the anion salts of alkali metals, and methods for preparing the same, of the invention and are not to be taken as limiting the scope of the invention.

EXAMPLE I

The sodium anion salt of sodium cation in a bicyclic polyoxadiamine was prepared by placing about 1 gram of 2,2,2-crypt in chamber one of a two-chamber vessel in which the chambers are joined by a side arm divided by a coarse frit. Chamber two contained a second side arm into which a capillary tube containing sodium metal had been inserted and sealed. The entire vessel was evacuated to about $10^{-6}$ Torr and the sodium was distilled into chamber two and the capillary tube sealed off under vacuum. Anhydrous ethylamine which had been dried first over calcium hydride and then over an alloy of sodium and potassium was distilled into chamber one by cooling the chamber with a dry-ice and isopropanol bath. The quantity of ethylamine used depends upon the amount of bicyclic compound present, and the quantity was adjusted to yield a 0.2 M metal dissolving solution. When solution was complete, it was transferred through the frit into chamber two containing the sodium. Upon contact, a dark blue solution formed immediately. The contact with the sodium was maintained with shaking for several minutes at temperatures between 0° and −60° C. The solution was then warmed to 0 to 10° C. and allowed to filter through the frit by cooling chamber one. Upon cooling to dry-ice temperature, gold-colored crystals of the sodium anion salt were formed. The supernatant liquid was again poured into chamber two to ensure that all of the metal which could be dissolved was in solution. Since sodium is insoluble in ethylamine in the absence of the complexant, the solubilization stopped when all of the free complexing agent had been used up.

After the final crystallization process, the supernatant solution was poured into chamber two, the vessel was again connected to a vacuum line and all of the ethylamine was removed by distillation. Then diethyl ether, $C_2H_5OC_2H_5$, which had been purified over $CaH_2$ and over benzophenone ketyl (benzophenone with an excess of Na-K alloy) was distilled into the vessel. The crystals of NaC+·Na− are only very slightly soluble in diethyl ether, which therefore serves as a convenient washing solvent. The light blue solution formed from the crystals in the presence of diethyl ether was poured off the crystals into chamber two and then distilled back into chamber one. This was repeated several times until all traces of blue were removed from the crystals. After removal of the diethyl ether by distillation, the vessel could be opened or broken in an inert-atmosphere box for removal of the crystals.

The identity was established by elemental analysis, decomposition with water and collection of the hydrogen evolved, titration with acid of the decomposed crystals and finally a complete X-ray structure determination.

In order to ascertain the composition of the material, a number of tests were conducted. A proton nuclear magnetic resonance study of the compound was made by dissolving some of the washed gold-colored solid sample in deuterated ammonia. The nuclear magnetic resonance (NMR) spectrum of the dark blue solution formed gave the pattern of the 2,2,2-crypt — an overlapped singlet and triplet downfield and a triplet upfield. The integrated signal gave a ratio of 2 to 1 for the combined triplet and singlet to the other triplet. The compound was thermally decomposed in vacuo and then opened in air. Deuterated chloroform was used as a solvent. The NMR spectrum obtained was the same, both in pattern and location, as that obtained with a solution of a sodium salt in the presence of 2,2,2-crypt.

The results of an elementary analysis of two samples of the sodium crystal solid are given in Table I below.

TABLE I

| Sample No. | % C | % H | % N | % Na |
|---|---|---|---|---|
| 1 | 51.04 | 8.56 | 6.62 | 11.17 |
| 2 | 51.21 | 8.68 | 6.77 | 10.92 |
| Average | 51.13 | 8.62 | 6.70 | 11.05 |
| Calculated Value Based on Formula $Na_2C_{18}H_{36}N_2O_6$ | 51.18 | 8.53 | 6.64 | 10.90 |

The reducing power of the compound was determined by decomposing the solid with degassed conductance water and collecting the hydrogen evolved by the reaction. The reducing power was calculated from the amount of hydrogen gas collected by assuming ideal gas behavior. With the technique used, 0.95 and 0.94 ± 0.03 mole of $H_2$ per mole of compound were formed in two separate experiments. The theoretical value of 1.0 is expected on the basis of two available electrons per molecule.

The sodium 2,2,2-crypt was very sensitive to air, forming a white solid in seconds. However, a sample in an evacuable dry box filled with dry helium or even flushed with nitrogen was stable with a shiny surface for at least a few minutes. A sample opened under a nonoxidizable dry solvent such as diethyl ether would remain unchanged for hours. The solid is stable at room temperature under vacuum and will decompose at about 83° C. As the temperature is raised from that of liquid nitrogen to decomposition temperature, a gradual color change from bright gold color to dark brown color was observed. Above the decomposition temperature, a white color mixed with gray spots was seen. After the solid has been decomposed at ∼83° C., it would redissolve back into ethylamine to form a dark blue solution. It is believed that the solid decomposed at least partially into 2,2,2-crypt and solid sodium at ∼83° C.

Single crystal X-ray diffraction studies showed the space group is R32 with three molecules per unit cell (hexagonal axes). Refinement of the structure (R = 0.085) gives the information that:

1. One of the sodium species is trapped in the crypt with interatomic distances which are very close to those having been reported for a similar structure with an iodide anion.

2. The other sodium species is outside of the crypt at a large distance from the other atoms. For example, the amine nitrogen is at 5.55 Å and the closest oxygen is at 5.76 Å. The logical conclusion is that the outside sodium is negatively charged.

EXAMPLE II

Another anion salt was prepared from a solution produced by the method of Example 1 except that rubidium metal was substituted for the sodium metal. The gold-colored crystals were in this case recovered by evaporating the solvent by low-temperature vacuum distillation at about −30° C. The optical absorption spectrum of the solution from which the compound was formed showed a Rb− peak leading to the conclusion that a rubidium anion salt of a rubidium cation of the bicyclic polyoxadiamine compound had been formed.

EXAMPLE III

Still another anion salt was prepared from a solution produced by the method of Example I except that a sodium-potassium alloy was substituted for sodium. Greenish-gold-colored crystals were recovered by evaporation of the solvent by low-temperature vacuum distillation at about −30° C. The optical absorption spectrum of the solution from which this compound was formed showed a Na− peak, the same as was obtained with the compound of Example I. Since it is known that the bicyclic compound prefers the potassium cation over the sodium cation, the conclusion is reached that a sodium anion salt of a potassium cation of the bicyclic polyoxadiamine compound had been formed.

As can be seen by the foregoing description and examples, the alkali metal anion salts of alkali metal cations of bicyclic polyoxadiamine compounds of this invention are unique compounds having an interesting utility as a two-electron reducing agent.

The embodiments of the invention in which an exclusive property or privilege is claimed are defined as follows:

1. A compound of an alkali metal anion salt of an alkali metal cation in a bicyclic polyoxadiamine compound of the formula:

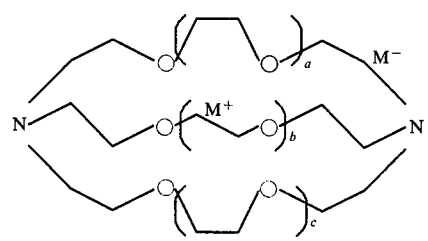

where M+ is a cation of an alkali metal, M− is an anion of an alkali metal, said M+ and M− are selected from the group consisting of Na, K, Rb, and Na and K, and $a$, $b$ and $c$ are integers from 0 to 2.

2. A compound of claim 1 wherein $a$, $b$ and $c$ are 1.

3. The compound of claim 2 wherein $M^+$ and $M^-$ are Na.

4. The compound of claim 2 wherein $M^+$ and $M^-$ are Rb.

5. The compound of claim 2 wherein $M^+$ is K and $M^-$ is Na.

6. A method for preparing an alkali metal anion salt of an alkali metal cation in a bicyclic polyoxadiamine compound comprising: dissolving bicyclic polyoxadiamine compound having the formula:

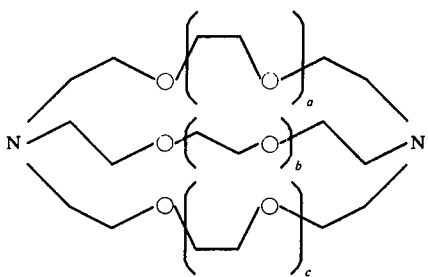

where $a$, $b$ and $c$ are integers from 0 to 2, in a suitable solvent, said solvent being a nonreactive, donor solvent having a dielectric constant from 8 to 20, to form a metal dissolving solution, containing up to about 0.2 M bicyclic polyoxadiamine compound, cooling the dissolving solution to below 10° C., contacting the cooled metal dissolving solution with an excess of an alkali metal until the solution is saturated with alkali metal, said alkali metal being selected from the group consisting of Na, K, Rb and Na and K, warming the solution to 0° to 10° C., whereby the anion salt is formed, separating the solvent solution from the alkali metal, and recovering the alkali metal anion salt of the alkali metal cation in a bicyclic polyoxadiamine compound.

7. The method of claim 5 wherein the solvent is selected from the group consisting of methylamine, ethylamine, ethylenediamine, tetrahydrofuran, 1,2-propane diamine and 1,3 propane diamine.

8. The method of claim 7 wherein a, b and c of the bicyclic compound are 1, the alkali metal is sodium and the sodium anion salt is recovered by cooling the metal dissolving solution saturated with sodium to below about $-15°$ C., whereby the sodium anion salt of a sodium cation precipitates from the metal dissolving solution, and filtering the solution to recover the salt.

9. The method of claim 6 wherein the anion salt is formed and recovered under a vacuum.

* * * * *